United States Patent [19]

Fischer et al.

[11] Patent Number: 5,069,711

[45] Date of Patent: Dec. 3, 1991

[54] HERBICIDAL N-ARYL-SUBSTITUTED NITROGEN-CONTAINING HETEROCYCLES

[75] Inventors: Reiner Fischer, Monheim; Uta Jensen-Korte, Duesseldorf; Franz Kunisch, Odenthal; Albrecht Marhold, Leverkusen; Pieter Ooms, Krefeld; Otto Schallner, Monheim; Hans-Joachim Santel, Leverkusen; Robert R. Schmidt, Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 649,101

[22] Filed: Feb. 1, 1991

Related U.S. Application Data

[62] Division of Ser. No. 419,809, Oct. 11, 1989.

[30] Foreign Application Priority Data

Oct. 15, 1988 [DE] Fed. Rep. of Germany ....... 3835168

[51] Int. Cl.$^5$ ................... A01N 43/48; A01N 43/36; C07D 471/02; C07D 211/22
[52] U.S. Cl. .......................... 71/92; 71/95; 514/299; 546/121
[58] Field of Search ............ 546/121, 240; 71/92, 71/95; 514/299

[56] References Cited

U.S. PATENT DOCUMENTS 4,919,704  4/1990  Moser et al. .............. 548/513

FOREIGN PATENT DOCUMENTS 0061741  10/1982  European Pat. Off. ............ 548/476
0083055  7/1983  European Pat. Off. ............ 548/476
0303573  2/1987  European Pat. Off. ............ 548/545

Primary Examiner—Mary C. Lee
Assistant Examiner—Joseph K. McKane
Attorney, Agent, or Firm—Sprung Horn Kramer & Woods

[57] ABSTRACT

Herbicidal N-aryl-substituted nitrogen-containing heterocycles of the formula

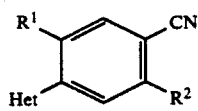 (I)

in which
Het represents a heterocycle of the formula

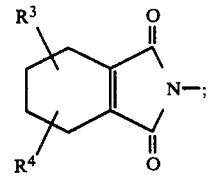

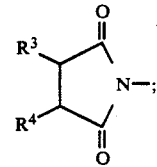

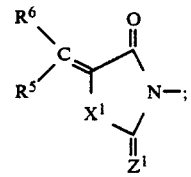

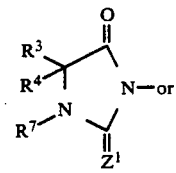

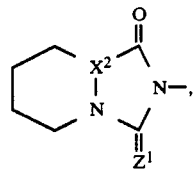

$R^1$ represents hydrogen or halogen and
$R^2$ represents halogen, hydroxyl or represents a radical $-Z^2-R^8$,
where
$X^1$ represents oxygen, represents a $-CH_2-$ group, represents a

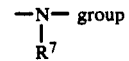

group or represents a

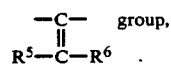

represents nitrogen or a CH group,
$Z^1$ represents oxygen or sulphur,
$Z^2$ represents oxygen or sulphur,
$R^3$ and $R^4$ independently of one another in each case represent hydrogen or alkyl,
$R^3$ and $R^6$ either independently of one another in each case represent hydrogen or alkyl or together represent a double-linked alkanediyl radical,
$R^7$ represents hydrogen, alkyl or represents optionally substituted aryl and
$R^8$ represents in each case optionally substituted alkyl, alkenyl alkinyl or cycloalkyl.

14 Claims, No Drawings

HERBICIDAL N-ARYL-SUBSTITUTED NITROGEN-CONTAINING HETEROCYCLES

This is a division of application Ser. No. 419,809, filed Oct. 11, 1989, now pending.

The invention relates to novel N-aryl-substituted nitrogen-containing heterocycles, several processes for their preparation, and their use as herbicides.

It is already known that certain N-aryl-substituted nitrogen-containing heterocycles, such as, for example, N-(2-fluoro-4-chloro-5-propargyloxy-phenyl)-$\Delta^1$-tetrahydrophthalimide, possess herbicidal properties (cf. European Patent 83,055 or European Patent 61,741).

However, the herbicidal activity of these previously known compounds against problem weeds, as well as their tolerance by certain crop plants, is not entirely satisfactory in all fields of application.

Furthermore EP-A 303 573 (publication date Feb. 15, 1989) which was not published prior to the priority date of Oct. 10, 1988 of the present application describes pyrrolidin-2,5-diones and 4,5,6,7,-tetrahydroisoindol-1,3-diones with herbicidal activity.

Novel N-aryl-substituted nitrogen-containing heterocycles of the general formula (I)

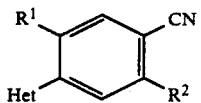 (I)

in which

Het represents a heterocycle of the formula

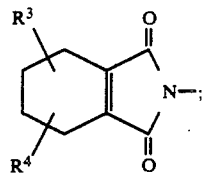

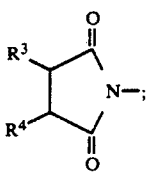

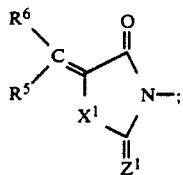

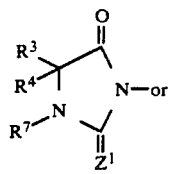

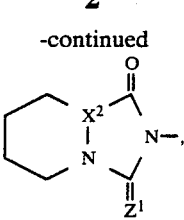

$R^1$ represents hydrogen or halogen and
$R^2$ represents halogen, hydroxyl or represents a radical $-Z^2-R^8$,
where
$X^1$ represents oxygen, represents a $-CH_2-$ group, represents a

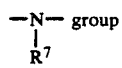 group or represents a

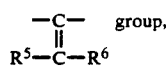 group, $X^2$ represents nitrogen or a CH group,
$Z^1$ represents oxygen or sulphur,
$Z^2$ represents oxygen or sulphur,
$R^3$ and $R^4$ independently of one another in each case represent hydrogen or alkyl,
$R^5$ and $R^6$ either independently of one another in each case represent hydrogen or alkyl or together represent a double-linked alkanediyl radical,
$R^7$ represents hydrogen, alkyl or represents optionally substituted aryl and
$R^8$ represents in each case optionally substituted alkyl, alkenyl, alkinyl or cycloalkyl,
have been found.

Furthermore, it has been found that the novel N-aryl-substituted nitrogen-containing heterocycles of the general formula (I)

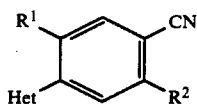 (I)

in which
Het represents a heterocycle of the formula

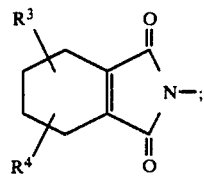

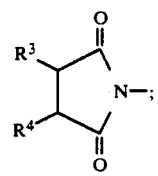

-continued

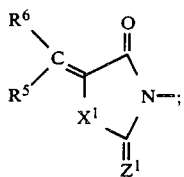

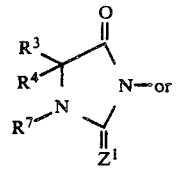

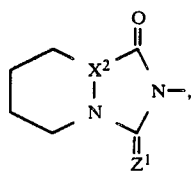

R¹ represents hydrogen or halogen and
R² represents halogen, hydroxyl or represents a radical —Z²—R⁸,
where
X¹ represents oxygen, represents a —CH₂— group, represents a

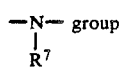

or represents a

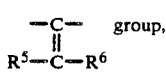

X² represents nitrogen or a CH group,
Z¹ represents oxygen or sulphur,
Z² represents oxygen or sulphur,
R³ and R⁴ independently of one another in each case represent hydrogen or alkyl,
R⁵ and R⁶ either independently of one another in each case represent hydrogen or alkyl or together represent a double-linked alkanediyl radical,
R⁷ represents hydrogen, alkyl or represents optionally substituted aryl and
R⁸ represents in each case optionally substituted alkyl, alkenyl, alkinyl or cycloalkyl, are obtained by one of the processes described below:
(a) N-aryl-substituted nitrogen-containing heterocycles of the formula (Ia)

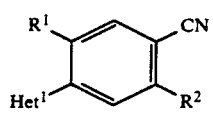

in which
Het¹ represents a heterocycle of the formula

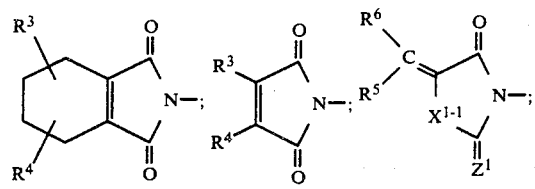

where
X¹⁻¹ represents a —CH₂— group or represents a

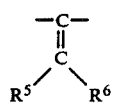

group and
R¹, R², R³, R⁴, R⁵ and R⁶ have the above-mentioned meanings,
are obtained when anhydrides of the formula (II)

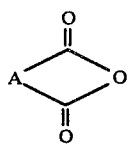

in which
A represents a radical of the formula

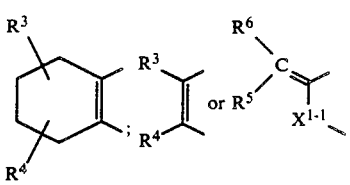

where
X¹⁻¹, R³, R⁴, R⁵ and R⁶ have the above-mentioned meanings,
are reacted with amines of the formula (III)

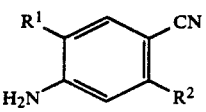

in which
R¹ and R² have the above-mentioned meanings,
if appropriate in the presence of a diluent and if appropriate in the presence of a reaction auxiliary;
(b) N-aryl-substituted nitrogen-containing heterocycles of the formula (Ib)

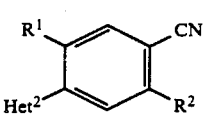

in which
Het² represents a heterocycle of the formula

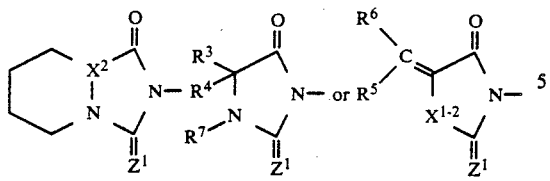

where
$X^{1-2}$ represents oxygen or a

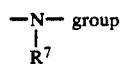

and
$R^1$, $R^2$, $R^3$, $R^4$, $R^5$, $R^6$, $R^7$, $X^2$ and $Z^1$ have the above-mentioned meanings,
are obtained when carboxylic acid esters of the formula (IV)

$$R^9-COOR^{10} \qquad (IV)$$

in which
$R^9$ represents a radical of the formula

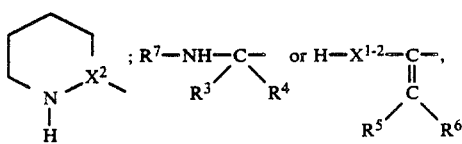

and
$R^{10}$ represents alkyl, where
$X^{1-2}$, $X^2$, $R^3$, $R^4$, $R^5$, $R^6$ and $R^7$ have the above-mentioned meanings,
or the acid addition salts thereof are reacted with iso(thio)cyanates of the formula (V)

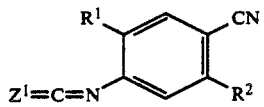

p10 in which
$R^1$, $R^2$ and $Z^1$ have the above-mentioned meanings,
if appropriate in the presence of a diluent and if appropriate in the presence of a reaction auxiliary;
(c) N-aryl-substituted nitrogen-containing heterocycles of the formula (Ic)

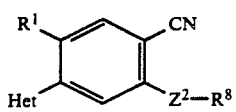

in which
$R^1$, $R^8$, $Z^2$ and Het have the above-mentioned meanings,
are obtained when the N-aryl-substituted nitrogen-containing heterocycles, which are obtainable by processes (a) and (b), of the formula (If)

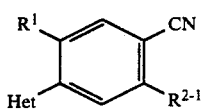

in which
$R^{2-1}$ represents halogen and
Het and $R^1$ have the above-mentioned meanings,
are reacted with alcohols or thiols of the formula (VI)

$$R^8-Z^2H \qquad (VI)$$

in which
$R^8$ and $Z^2$ have the above-mentioned meanings,
if appropriate in the presence of a diluent and in the presence of a reaction auxiliary;
(d) N-aryl-substituted nitrogen-containing heterocycles of the formula (Id)

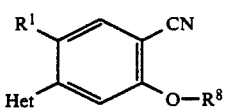

in which
$R^1$, $R^8$ and Het have the above-mentioned meanings,
are obtained when N-aryl-substituted nitrogen-containing heterocycles of the formula (Ie)

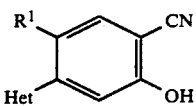

in which
$R^1$ and Het have the above-mentioned meanings,
are reacted with alkylating agents of the formula (VII)

$$R^8-E \qquad (VII)$$

in which
E represents an electron-withdrawing leaving group and
$R^8$ has the above-mentioned meaning, if appropriate in the presence of a diluent and if appropriate in the presence of a reaction auxiliary;
(e) N-aryl-substituted nitrogen-containing heterocycles of the formula (Ie)

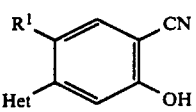

in which
$R^1$ and Het have the above-mentioned meanings,
are obtained when
e-α) N-aryl-substituted nitrogen-containing heterocycles of the formula (Ig)

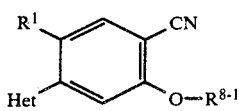 (Ig)

in which
R$^{8-1}$ represents allyl or benzyl and
R$^1$ and Het have the above-mentioned meanings,
are, in the event that R$^{8-1}$ represents benzyl, reacted with reducing agents, if appropriate in the presence of a catalyst and if appropriate in the presence of a diluent and if appropriate in the presence of a reaction auxiliary, and, in the event that R$^{8-1}$ represents allyl, are reacted with noble-metal catalysts followed by splitting off under acid conditions, if appropriate in the presence of a diluent, or when p1 e-β) amines of the formula (IIIa)

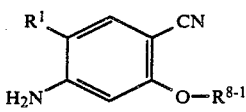 (IIIa)

in which
R$^1$ and R$^{8-1}$ have the above-mentioned meanings, are, in the event that R$^{10}$ represents benzyl, reacted with reducing agents, if appropriate in the presence of a catalyst and if appropriate in the presence of a diluent and if appropriate in the presence of a reaction auxiliary, and, in the event that R$^{10}$ represents allyl, are reacted with noble-metal catalysts followed by splitting off under acid conditions, if appropriate in the presence of a diluent, and the resulting aminophenols of the formula (VIII)

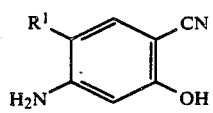 (VIII)

in which
R$^1$ has the above-mentioned meaning,
are reacted with anhydrides of the formula (II)

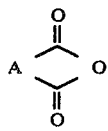 (II)

in which
A represents a radical of the formula

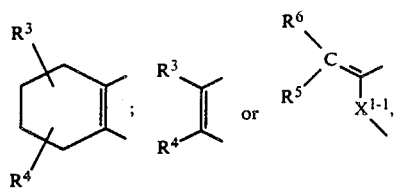

where
X$^{1-1}$ represents a —CH$_2$— group or represents a

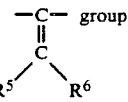 group and
R$^3$, R$^4$, R$^5$ and R$^6$ have the above-mentioned meanings,
if appropriate in the presence of a diluent and if appropriate in the presence of a reaction auxiliary.

Finally, it has been found that the novel N-aryl-substituted nitrogen-containing heterocycles of the general formula (I) possess herbicidal properties. Moreover, the compounds of the formula (I) in which R$^2$ represents hydroxyl are also suitable as valuable intermediates for N-aryl-substituted nitrogen-containing heterocycles of the formula (I) according to the invention.

Surprisingly, the N-aryl-substituted nitrogen-containing heterocycles of the general formula (I) according to the invention show a comparable herbicidal activity towards important problem weeds compared with the N-aryl-substituted nitrogen-containing heterocycles which are known from the prior art, such as, for example, N-(2-fluoro-4-chloro-5-propargyloxy-phenyl)-Δ$^1$-tetrahydrophthalimide, which are chemically similar compounds of a similar type of action, while simultaneously having a markedly improved tolerance by important crop plants.

Formula (I) provides a general definition of the N-aryl-substituted nitrogen-containing heterocycles according to the invention.

Preferred compounds of the formula (I) are those in which
Het represents a heterocycle of the formula

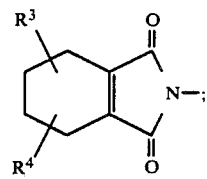

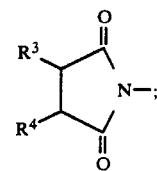

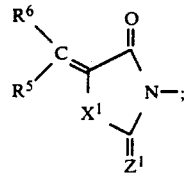

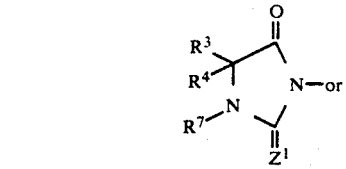

-continued

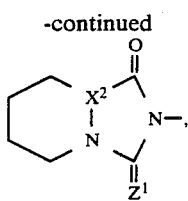

R[1] represents hydrogen, fluorine, chlorine or bromine and

R[2] represents fluorine, chlorine, bromine, hydroxyl, or represents a radical —Z[2]—R[8], where X[1] represents oxygen, represents a —CH$_2$— group, represents a

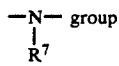

or represents a

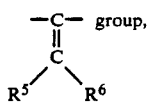

X[2] represents nitrogen or a —CH— group,

Z[1] represents oxygen or sulphur,

Z[2] represents oxygen or sulphur,

R[3], and R[4] independently of one another in each case represent hydrogen or represent straight-chain or branched alkyl having 1 to 4 carbon atoms, R[5] and R[6] either independently of one another in each case represent hydrogen or represent straight-chain or branched alkyl having 1 to 4 carbon atoms, or together represent a double-linked alkanediyl radical having 2 to 7 carbon atoms, R[7] represents hydrogen, represents straight-chain or branched alkyl having 1 to 4 carbon atoms or represents phenyl which is optionally monosubstituted or polysubstituted by identical or different substituents, suitable substituents in each case being: halogen, cyano, nitro, in each case straight-chain or branched alkyl, alkoxy or alkylthio, each having 1 to 4 carbon atoms, and also in each case straight-chain or branched halogenoalkyl, halogenoalkoxy or halogenoalkylthio, each having 1 to 4 carbon atoms and 1 to 9 identical or different halogen atoms and R[8] represents in each case straight-chain or branched alkyl having 1 to 8 carbon atoms, alkenyl having 2 to 8 carbon atoms, alkinyl having 3 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 3 to 8 carbon atoms and 1 to 13 identical or different halogen atoms, cyanoalkyl, alkoxyalkyl, alkylthioalkyl, halogenoalkoxyalkyl, alkoxyalkoxyalkyl, bis-(alkoxy)alkyl, bis-(alkythio)alkyl, alkylcarbonylalkyl, alkoxycarbonylakyl or alkoxyalkoxycarbonylalkyl, each having 1 to 8 carbon atoms in the individual alkyl moieties and if appropriate 1 to 9 identical or different halogen atoms, or represents cycloalkyl, cycloalkyloxycarbonylalkyl or cycloalkylalkyl, each of which has 3 to 7 carbon atoms in the cycloalkyl moiety and if appropriate 1 to 4 carbon atoms in the straight-chain or branched alkyl moiety and each of which is optionally monosubstituted or polysubstituted by identical or different substituents, suitable substituents in the cycloalkyl moiety in each case being: halogen as well as in each case straight-chain or branched alkyl or alkoxy, each having 1 to 4 carbon atoms, R[8] furthermore also represents oxetanylalkyl, tetrahydrofuranylalkyl or tetrahydropyranylalkyl, each of which has 1 to 3 carbon atoms in the respective alkyl moieties and each of which is optionally substituted by alkyl having 1 to 4 carbon atoms, and finally represents aralkyl which has 6 to 10 carbon atoms in the aryl moiety and 1 to 4 carbon atoms in the straight-chain or branched alkyl moiety and is optionally mono-substituted or poly-substituted by identical or different substituents, possible aryl substituents being: halogen, cyano, nitro, in each case straight-chain or branched alkyl, alkoxy, alkylthio or alkoxycarbonyl, each having 1 to 4 carbon atoms, or in each case straight-chain or branched halogenoalkyl, halogenoalkoxy or halogenoalkylthio, each having 1 to 4 carbon atoms and 1 to 9 identical or different halogen atoms.

A particularly preferred group of compounds of the formula (I) is that in which

Het represents a heterocycle of the formula

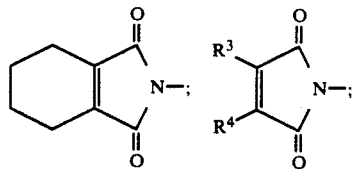

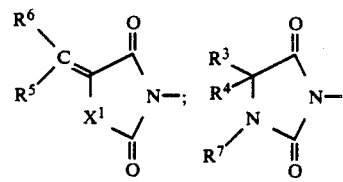

or

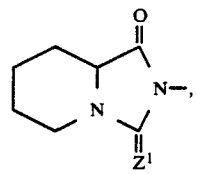

R[1] represents hydrogen, fluorine or chlorine and

R[2] represents fluorine, chlorine or represents a radical —Z[2]—R[8],

X[1] represents a —CH$_2$— group, represents a

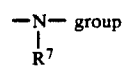

group or represents a

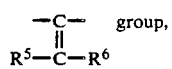

$Z^1$ represents oxygen or sulphur,
$Z^2$ represents oxygen or sulphur,
$R^3$ and $R^4$ independently of one another in each case represent hydrogen, methyl, ethyl, n- or i-propyl,
$R^5$ and $R^6$ either independently of one another in each case represent hydrogen, methyl, ethyl, n- or i-propyl, or together represent a double-linked alkanediyl radical having 2 to 5 carbon atoms,
$R^7$ represents hydrogen, methyl, ethyl, n- or i-propyl, or represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or r-butyl, methoxy, ethoxy, n- or i-propoxy, methylthio, trifluoromethyl, trifluoromethoxy or trifluoromethylthio and
$R^8$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, furthermore represents in each case straight-chain or branched halogenoalkyl having 1 to 4 carbon atoms or halogenoalkenyl having 3 to 5 carbon atoms and in each case 1 to 8 identical or different halogen atoms, in particular fluorine, chlorine or bromine, or represents in each case straight-chain or branched cyanoalkyl, alkoxyalkyl, alkylthioalkyl, halogenoalkoxyalkyl, alkoxyalkoxyalkyl, alkylcarbonylalkyl, alkoxycarbonylalkyl or alkoxyalkoxycarbonylalkyl, each having 1 to 5 carbon atoms in the individual alkyl moieties, furthermore represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, in each case optionally monosubstituted to trisubstituted by identical or different substituents from the series comprising methyl, methoxy, fluorine or chlorine, or represents oxetanylmethyl, oxetanylethyl, tetrahydrofuranylmethyl, tetrahydrofuranylethyl, tetrahydropyranylmethyl or tetrahydropyranylethyl, in each case optionally substituted by methyl and/or ethyl, or represents benzyl or phenylethyl, in each case optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy or trifluoromethylthio.

Another particularly preferred group of compounds of the formula (I) is that in which $R^2$ represents hydroxyl and the remaining radicals have the meaning mentioned above as being particularly preferred. Very particularly preferred is the group of compounds of the formula (I) in which Het represents a heterocycle of the formula

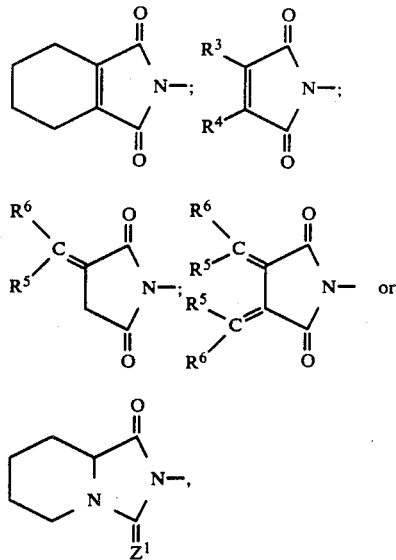

$R^1$ represents fluorine and
$R^2$ represents fluorine or represents a radical $-Z^2-R^8$, where
$Z^2$ represents oxygen or sulphur.
$R^3$ and $R^4$ independently of one another in each case represent hydrogen or methyl,
$R^5$ and $R^6$ either independently of one another each represent hydrogen or methyl, or together represent an ethane-1,2-diyl radical, a butane-1,4-diyl radical or a pentane-1,5-diyl radical and
$R^8$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, furthermore represents in each case straight-chain or branched halogenoalkyl having 1 to 4 carbon atoms or halogenoalkenyl having 3 to 5 carbon atoms and in each case 1 to 5 identical or different halogen atoms, in particular fluorine, chlorine or bromine, or represents in each case straight-chain or branched cyanoalkyl, alkoxyalkyl, alkoxyalkoxyalkyl or alkoxycarbonylalkyl, each having 1 to 5 carbon atoms in the individual alkyl moieties, moreover represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, in each case optionally monosubstituted or trisubstituted by identical or different substituents from the series comprising methyl, methoxy, fluorine or chlorine, or represents oxetanylmethyl, oxetanylethyl, tetrahydrofuranylmethyl or tetrahydropyranylmethyl, in each case optionally substituted by methyl or ethyl, or represents benzyl or phenylethyl, in each case optionally monosubstituted to trisubstituted by identical or different substituents, suitable substituents in each case being:
fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy or trifluoromethylthio.

Another very particularly preferred group of compounds of the formula (I) is that in which R² represents hydroxyl and the remaining radicals have the meaning mentioned above as being very particularly preferred.

The following N-aryl-substituted nitrogen-containing heterocycles of the general formula (I) may be mentioned individually in addition to the compounds mentioned in the Preparation Examples:

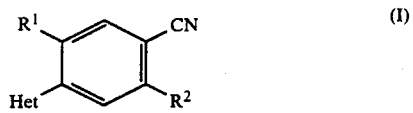

| Het | R¹ | R² |
|---|---|---|
| ![tetrahydrophthalimide] | F | —O—CH₂—C≡CH |
| ![piperidine-fused hydantoin] | F | —O—CH₂—C≡CH |
| ![dimethylmaleimide] | F | —O—CH₂—C≡CH |
| ![isopropylidene succinimide] | F | —O—CH₂—C≡CH |
| ![triazinedione] | F | —O—CH₂—C≡CH |
| ![tetrahydrophthalimide] | H | —O—CH₂—C≡CH |
| ![piperidine-fused hydantoin] | H | —O—CH₂—C≡CH |

| Het | R¹ | R² |
|---|---|---|
| [bicyclic triazinedione, saturated 6-ring fused to 1,2,4-triazolidine-3,5-dione] | H | —O—CH₂—C≡CH |
| [3,4,5,6-tetrahydrophthalimide] | F | —O—CH(CH₃)—COOCH₃ |
| [3,4,5,6-tetrahydrophthalimide] | F | —S—CH₂—COOC₂H₅ |
| [3,4,5,6-tetrahydrophthalimide] | F | —S—CH(CH₃)₂ |
| [3,4,5,6-tetrahydrophthalimide] | F | —O—CH₂—C(=O)—CH₃ |
| [3,4,5,6-tetrahydrophthalimide] | F | —O—CH(CH₃)—CN |
| [3,4,5,6-tetrahydrophthalimide] | F | —O—CH₂—CH=CH₂ |
| [3,4,5,6-tetrahydrophthalimide] | F | —O—CH(CH₃)₂ |
| [bicyclic triazinedione, saturated 6-ring fused to 1,2,4-triazolidine-3,5-dione] | F | —S—CH(CH₃)—CN |

-continued

| Het | R¹ | R² |
|---|---|---|
| bicyclic pyridazine-1,2,4-triazine-3,5-dione (hexahydro) | F | —O—cyclopentyl |
| (same) | F | —O—CH₂—C(CH₃)₂—OC₂H₅ |
| (same) | F | —O—CH₂—CH(CH₃)—CH₂—SCH₃ |
| (same) | F | —O—CH₂—CH₂—O—CH(CH₂F)(CH₂F) |
| (same) | F | —O—CH₂—C₆H₅ |
| (same) | F | —S—CH₂—C₆H₄—Cl (4-) |
| hexahydroimidazo[1,2-a]pyridine-1,3-dione | F | —O—CH(CH₃)—COOCH₃ |
| (same) | F | —S—CH₂—COO—cyclopentyl |
| (same) | F | —S—CH₂—COO—(CH₂)₄—CH₃ |

-continued
| Het | R¹ | R² |
|---|---|---|
| 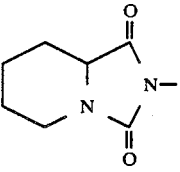 | F | —O—CH₂—CN |
| 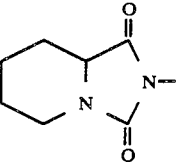 | F | —O—CH—C—CH₃<br>         \|     \|\|<br>        CH₃   O |
| 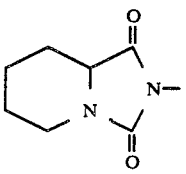 | F | —S—CH₂—CH=CH₂ |
| 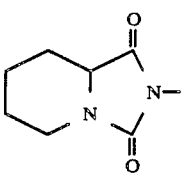 | F | —S—CH₂—C≡CH |
| 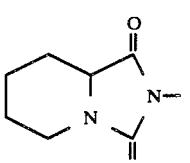 | F | —O—CH—COOC₂H₅<br>         \|<br>        C₂H₅ |
| 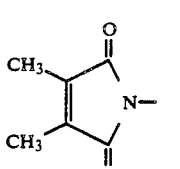 | F | $\quad\quad$ CF₃<br>$\quad\quad$ \|<br>—O—C=CH—CF₃ |
| 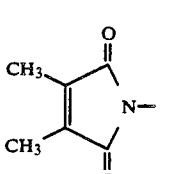 | F | —O—CH—CH₂—CF₃<br>         \|<br>        CF₃ |
| 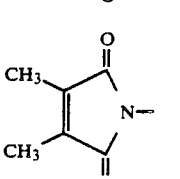 | F | —S—CH₂—CH=CH₂ |
| 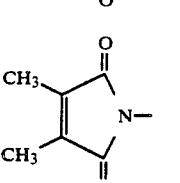 | F | $\quad\quad\quad$ CH₂F<br>$\quad\quad\quad$ /<br>—O—CH<br>$\quad\quad\quad$ \\<br>$\quad\quad\quad$ CH₂F |

-continued

| Het | R¹ | R² |
|---|---|---|
| 3,4-dimethyl-maleimide (N-) | F | $-S-CH_2-C\equiv CH$ |
| 3-isopropylidene-succinimide (N-) | F | $-O-CH(CH_3)_2$ |
| 3,4,5,6-tetrahydrophthalimide (N-) | F | $-S-CH(CH_3)-COOCH_3$ |
| 3,4,5,6-tetrahydrophthalimide (N-) | F | $-S-CH_2-COO-\text{cyclopentyl}$ |
| 3,4,5,6-tetrahydrophthalimide (N-) | F | $-S-CH_2-COO-(CH_2)_4-CH_3$ |
| 3,4,5,6-tetrahydrophthalimide (N-) | F | $-S-CH(C_2H_5)-COOC_2H_5$ |
| 3,4,5,6-tetrahydrophthalimide (N-) | H | $-S-CH(CH_3)-COOCH_3$ |
| 3,4,5,6-tetrahydrophthalimide (N-) | H | $-S-CH_2-COO-\text{cyclopentyl}$ |
| 3,4,5,6-tetrahydrophthalimide (N-) | H | $-S-CH_2-COO-(CH_2)_4-CH_3$ |

| Het | R¹ | R² |
|---|---|---|
| 2-(3,4,5,6-tetrahydrophthalimido) | H | —S—CH(C₂H₅)—COOC₂H₅ |
| hexahydro-pyrido-oxadiazinedione | H | —S—CH(CH₃)—COOC₂H₅ |
| hexahydro-triazinedione | H | —S—CH₂—C≡CH |
| 2-(3,4,5,6-tetrahydrophthalimido) | H | —O—CH(CH₃)—COOCH₃ |
| 2-(3,4,5,6-tetrahydrophthalimido) | H | —S—CH₂—COOC₂H₅ |
| 2-(3,4,5,6-tetrahydrophthalimido) | H | —S—CH(CH₃)₂ |
| 2-(3,4,5,6-tetrahydrophthalimido) | H | —O—CH₂—C(=O)—CH₃ |
| 2-(3,4,5,6-tetrahydrophthalimido) | H | —O—CH(CH₃)—CN |
| 2-(3,4,5,6-tetrahydrophthalimido) | H | —O—CH₂—CH=CH₂ |

| Het | R¹ | R² |
|---|---|---|
| [tetrahydrophthalimide ring] | H | —O—CH(CH$_3$)$_2$ |
| [hexahydroimidazo-pyridine-dione ring] | H | —O—CH(CH$_3$)—COOCH$_3$ |
| [hexahydroimidazo-pyridine-dione ring] | H | —S—CH$_2$—COO—cyclopentyl |
| [hexahydroimidazo-pyridine-dione ring] | H | —S—CH$_2$—COO—(CH$_2$)$_4$—CH$_3$ |
| [hexahydroimidazo-pyridine-dione ring] | H | —O—CH$_2$—CN |
| [hexahydroimidazo-pyridine-dione ring] | H | —O—CH(CH$_3$)—C(=O)—CH$_3$ |
| [hexahydroimidazo-pyridine-dione ring] | H | —S—CH$_2$—CH=CH$_2$ |
| [hexahydroimidazo-pyridine-dione ring] | H | —S—CH$_2$—C≡CH |
| [hexahydroimidazo-pyridine-dione ring] | H | —O—CH(C$_2$H$_5$)—COOC$_2$H$_5$ |

-continued
| Het | R¹ | R² |
|---|---|---|
| 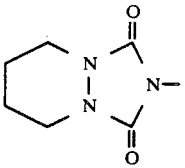 | H | 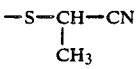 |
| 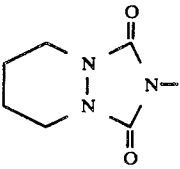 | H | 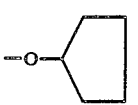 |
| 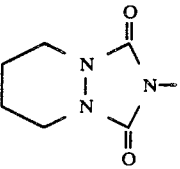 | H | 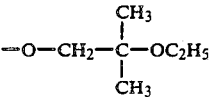 |
| 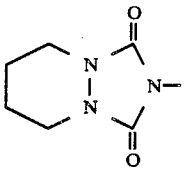 | H | 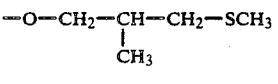 |
| 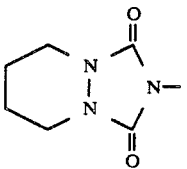 | H | 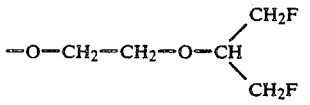 |
| 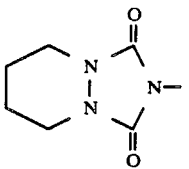 | H | 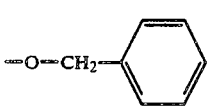 |
| 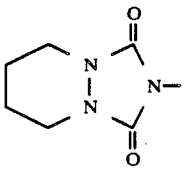 | H | 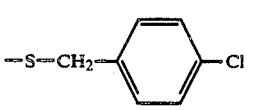 |
| 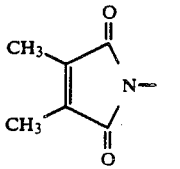 | H | 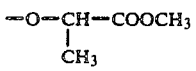 |
| 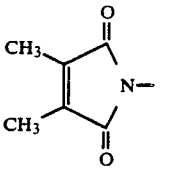 | H | 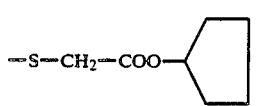 |

| Het | R¹ | R² |
|---|---|---|
| 3,4-dimethyl-maleimide | H | $-S-CH_2-COO-(CH_2)_4-CH_3$ |
| 3,4-dimethyl-maleimide | H | $-O-C(CF_3)=CH-CF_3$ |
| 3,4-dimethyl-maleimide | H | $-O-CH(CF_3)-CH_2-CF_3$ |
| 3,4-dimethyl-maleimide | H | $-S-CH_2-CH=CH_2$ |
| 3,4-dimethyl-maleimide | H | $-O-CH(CH_2F)_2$ |
| 3,4-dimethyl-maleimide | | $-S-CH_2-C\equiv CH$ |
| 3-isopropylidene-succinimide | H | $-S-CH(CH_3)-COOCH_3$ |
| 3-isopropylidene-succinimide | H | $-O-CH_2-C(CH_3)=CH_2$ |
| 3-isopropylidene-succinimide | H | $-O-CH(CH_3)_2$ |

| Het | R¹ | R² |
|---|---|---|
| 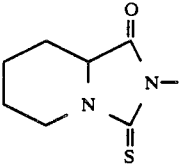 | F | —O—CH₂—C≡CH |
| 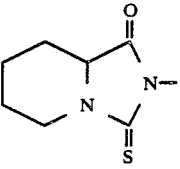 | F | —O—CH₂—CH=CH₂ |
| 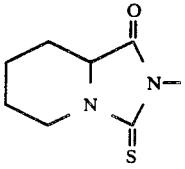 | F | —O—CH₂—CH₂—OCH₃ |
| 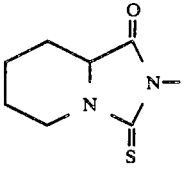 | F | —S—CH₂—COO—cyclopentyl |
| 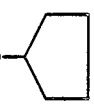 | F | —O—CH(CH₃)—COOC₂H₅ |
| 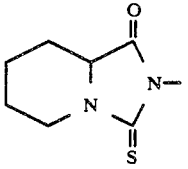 | F | —O—CH₂—COOC₂H₅ |
| 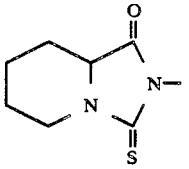 | F | —O—CH₂—COO—CH₂CH₂—O—CH₃ |
| 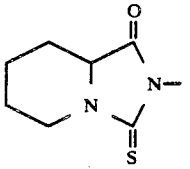 | F | —O—CH₂—CH₂—O—CH₂—CH₂—OC₂H₅ |
| 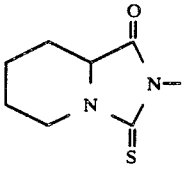 | F | —S—CH(CH₃)—COOC₂H₅ |

-continued
| Het | R¹ | R² |
|---|---|---|
| 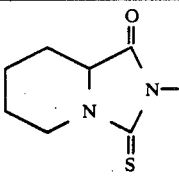 | F | —O—CH(CH₂F)₂ |
| 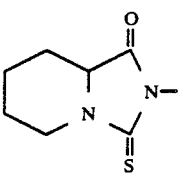 | F | —O—CH₂—CN |
| 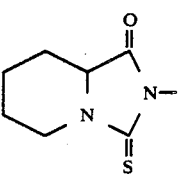 | F | —S—CH₂—CH=CH₂ |
| 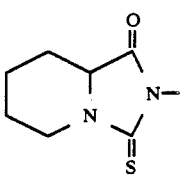 | F | —S—CH₂—C≡CH |
| 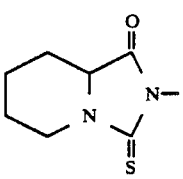 | F | —O—CH₂—COO—(CH₂)₃—CH₃ |
| 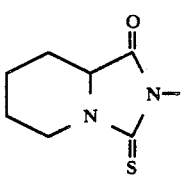 | H | —O—CH₂—C≡CH |
| 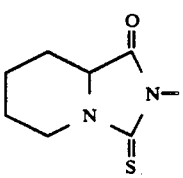 | H | —O—CH₂—CH=CH₂ |
| 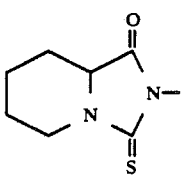 | H | —O—CH₂—CH₂—OCH₃ |
| 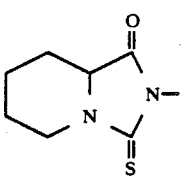 | H | —S—CH₂—COO—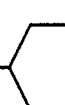 |

-continued
| Het | R¹ | R² |
|---|---|---|
| 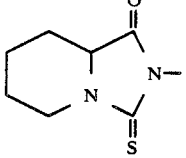 | H | —O—CH(CH₃)—COOC₂H₅ |
| 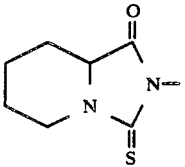 | H | —O—CH₂—COOC₂H₅ |
| 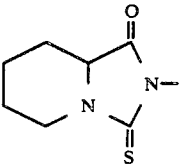 | H | —O—CH₂—COO—CH₂—CH₂—OCH₃ |
| 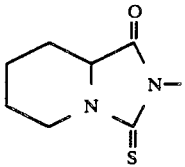 | H | —O—CH₂—CH₂—O—CH₂—CH₂—OC₂H₅ |
| 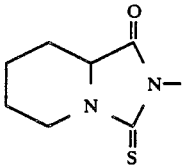 | H | —S—CH(CH₃)—COOC₂H₅ |
| 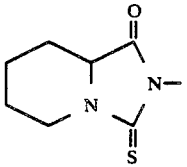 | H | —O—CH(CH₂F)₂ |
| 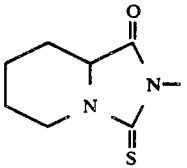 | H | —O—CH₂—CN |
| 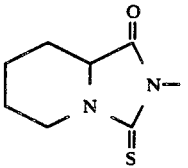 | H | —S—CH₂—CH=CH₂ |
| 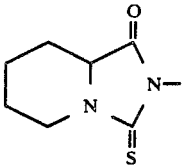 | H | —S—CH₂—C≡CH |

-continued
| Het | R¹ | R² |
|---|---|---|
| 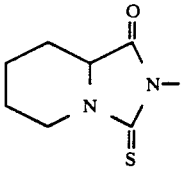 | H | —O—CH₂—COO—(CH₂)₃—CH₃ |
| 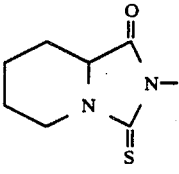 | Cl | —O—CH₂—C≡CH |
| 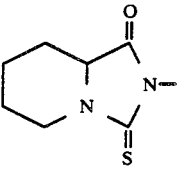 | Cl | —O—CH₂—CH=CH |
| 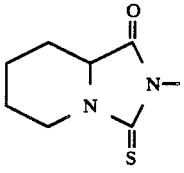 | Cl | —O—CH₂—CH₂—OCH₃ |
| 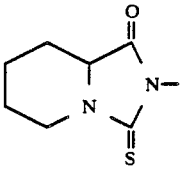 | Cl | —S—CH₂—COO—⟨cyclopentyl⟩ |
| 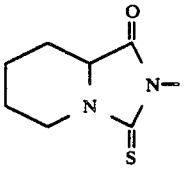 | Cl | —O—CH—COOC₂H₅<br>          \|<br>         CH₃ |
| 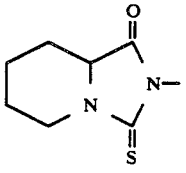 | Cl | —O—CH₂—COOC₂H₅ |
| 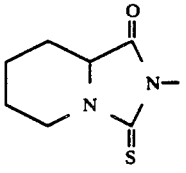 | Cl | —O—CH₂—COO—CH₂—CH₂—OCH₃ |
| 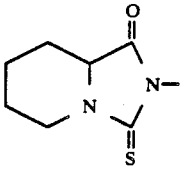 | Cl | —O—CH₂—CH₂—O—CH₂—CH₂—OC₂H₅ |

-continued
| Het | R¹ | R² |
|---|---|---|
| 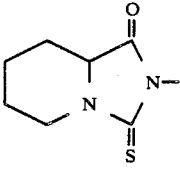 | Cl | —S—CH—COOC₂H₅<br>      \|<br>      CH₃ |
| 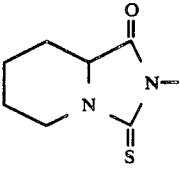 | Cl | —O—CH(CH₂F)₂ |
| 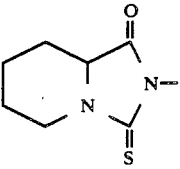 | Cl | —O—CH₂—CN |
| 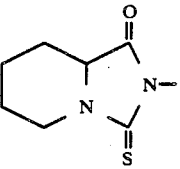 | Cl | —S—CH₂—CH=CH₂ |
| 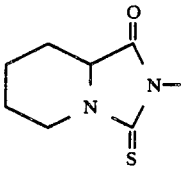 | Cl | —S—CH₂—C≡CH |
| 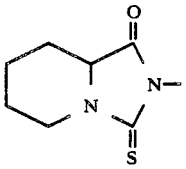 | Cl | —O—CH₂—COO—(CH₂)₃—CH₃ |
| 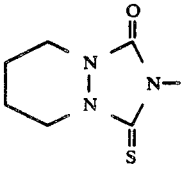 | H | —O—CH₂—C≡CH |
| 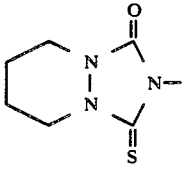 | H | —O—CH₂—CH=CH₂ |
| 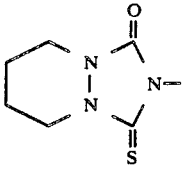 | H | —O—CH₂—CH₂—OCH₃ |

-continued
| Het | R¹ | R² |
|---|---|---|
| 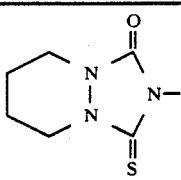 | H | —S—CH₂—COO—⌬ |
| 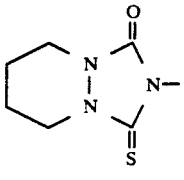 | H | —O—CH(CH₃)—COOC₂H₅ |
| 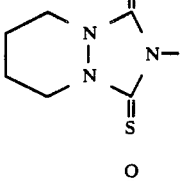 | H | —O—CH₂—COOC₂H₅ |
| 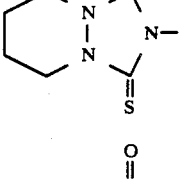 | H | —O—CH₂—COO—CH₂—CH₂—OCH₃ |
| 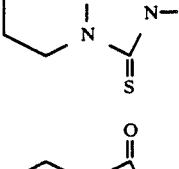 | H | —O—CH₂—CH₂—O—CH₂—CH₂—OC₂H₅ |
| 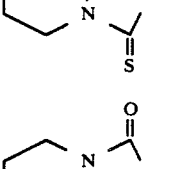 | H | —S—CH(CH₃)—COOC₂H₅ |
| 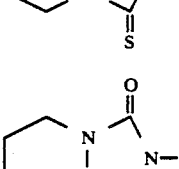 | H | —O—CH(CH₂F)₂ |
| 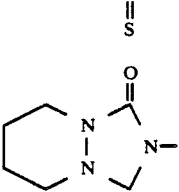 | H | —O—CH₂—CN |
|  | H | —S—CH₂—CH=CH₂ |

| Het | R¹ | R² |
|---|---|---|
| [bicyclic triazinone-thione ring] | H | —S—CH$_2$—C≡CH |
| [bicyclic triazinone-thione ring] | H | —O—CH$_2$—COO—(CH$_2$)$_3$—CH$_3$ |
| [bicyclic triazinone-thione ring] | F | —O—CH$_2$—C≡CH |
| [bicyclic triazinone-thione ring] | F | —O—CH$_2$—CH=CH$_2$ |
| [bicyclic triazinone-thione ring] | F | —O—CH$_2$—CH$_2$—OCH$_3$ |
| [bicyclic triazinone-thione ring] | F | —S—CH$_2$—COO—[cyclopentyl] |
| [bicyclic triazinone-thione ring] | F | —O—CH(CH$_3$)—COOC$_2$H$_5$ |
| [bicyclic triazinone-thione ring] | F | —O—CH$_2$—COOC$_2$H$_5$ |
| [bicyclic triazinone-thione ring] | F | —O—CH$_2$—COO—CH$_2$—CH$_2$—OCH$_3$ |

-continued

| Het | R¹ | R² |
|---|---|---|
| (tetrahydro-1,2,4-triazine with C=O and C=S) | F | $-O-CH_2-CH_2-O-CH_2-CH_2-OC_2H_5$ |
| (same) | F | $-S-CH(CH_3)-COOC_2H_5$ |
| (same) | F | $-O-CH(CH_2F)_2$ |
| (same) | F | $-O-CH_2-CN$ |
| (same) | F | $-S-CH_2-CH=CH_2$ |
| (same) | F | $-S-CH_2-C\equiv CH$ |
| (same) | F | $-O-CH_2-COO-(CH_2)_3-CH_3$ |

If, for example, 3,4,5,6-tetrahydrophthalic anhydride and 2,5-difluoro-4-aminobenzonitrile are used as starting substances, the course of the reaction of process (a) according to the invention may be represented by the following equation:

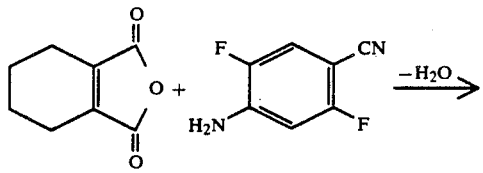

$\xrightarrow{-H_2O}$

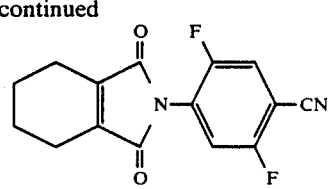

If, for example, ethyl 2-piperidinylcarboxylate and 4-cyano-3-methoxyphenyl isocyanate are used as starting substances, the course of the reaction of process (b) according to the invention may be represented by the following equation:

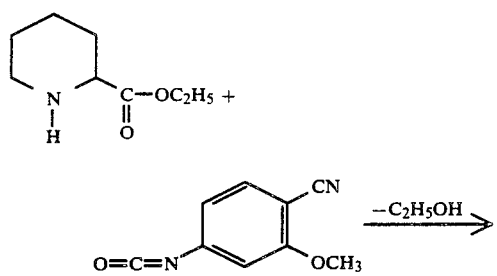

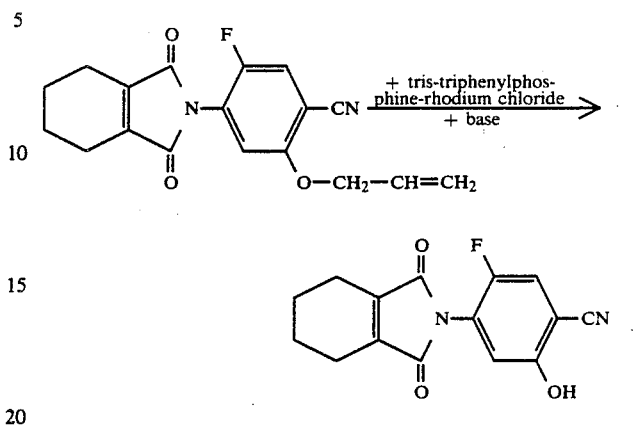

If, for example, N-(2,5-difluoro-4-cyanophenyl)-3,4-dimethyl-Δ³-pyrroline-2,5-dione and t-butylmercaptan are used as starting substances, the course of the reaction of process (c) according to the invention may be represented by the following equation:

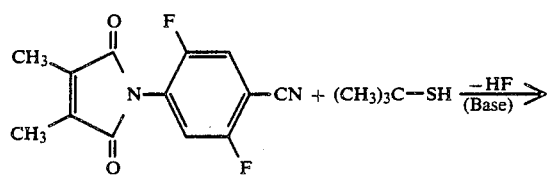

If, for example, 2-(4-cyano-2-fluoro-5-hydroxyphenyl)-hexahydroimidazo[1,5-a]pyridine-1,3dione and allyl bromide are used as starting substances, the course of the reaction of process (d) according to the invention may be represented by the following equation:

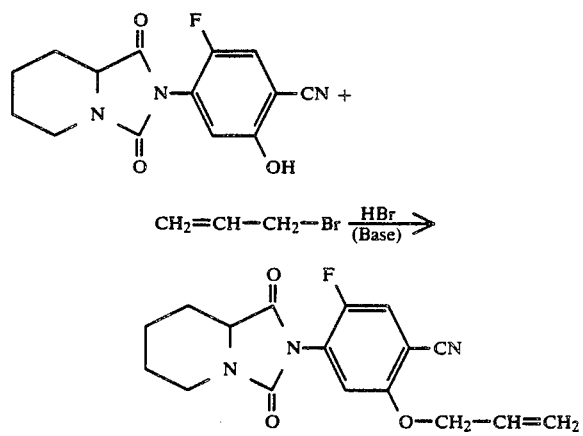

If, for example, N-(2-fluoro-4-cyano-5-allyloxyphenyl)-3,4,5,6-tetrahydrophthalimide is used as starting substance and tris-triphenylphosphine-rhodium chloride as reducing agent, the course of the reaction of process (e-α) according to the invention may be represented by the following equation:

If, for example, 2-allyloxy-4-amino-5-fluorobenzonitrile is used as starting substance and tris-triphenylphosphine-rhodium chloride as reducing agent in step 1 and tetrahydrophthalic anhydride as starting substance in step 2, the course of the reaction of process (e-β) according to the invention may be represented by the following equation:

Step 1

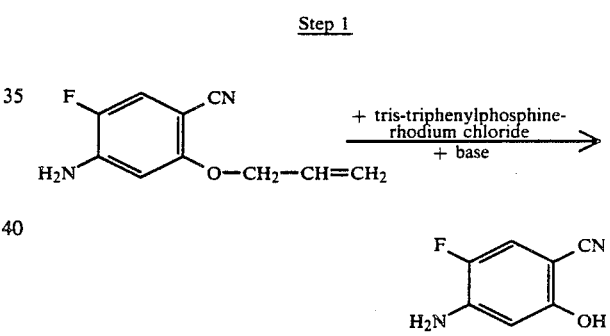

Step 2

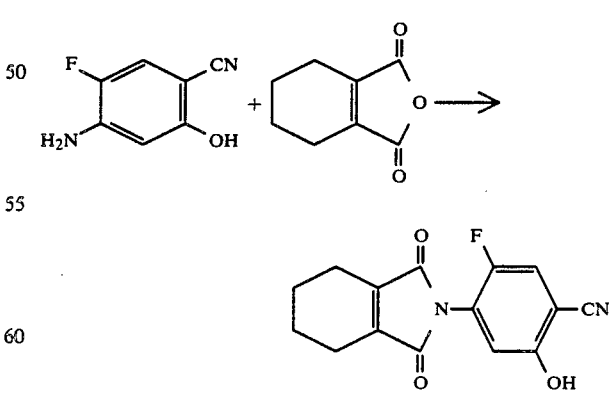

Formula (II) provides a general definition of the anhydrides required as starting substances for carrying out process (a) according to the invention. In this formula (II), A preferably represents a radical of the formula

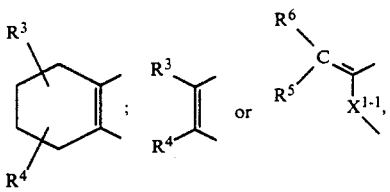

where
$X^{1-1}$ represents a —CH$_2$— group or represents a

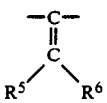

group and $R^3$, $R^4$, $R^5$ and $R^6$ preferably represent those radicals which have already been mentioned in connection with the description of the substances of the formula (1) according to the invention as being preferred for these substituents.

The anhydrides of the formula (II) are known or can be obtained in analogy to known processes (cf., for example, Gazz. chim. Ital. 57, 300-311 [1927]; DE-OS (German Published Specification) 3,644,222; J. org. Chem. 51, 4150-4158 [1986]; Tetrahedron Lett. 25, 6027-6030 [1984]; J. org. Chem. 42, 4162-4164 [1977]; Liebigs Ann. Chem. 1977, 772-790; Tetrahedron 25, 4099-4108 [1969]; and Japanese Patent 43/9046).

Formula (III) provides a general definition of the amines furthermore required as starting substances for carrying out process (a) according to the invention. In this formula (III), $R^1$ and $R^2$ preferably represent those radicals which have already been mentioned in connection with the description of the substances of the formula (I) according to the invention as being preferred for these substituents.

The amines of the formula (III) are known or can be obtained in analogy to known processes (cf., for example, European Patent 224,001; U.S. Pat. No. 4,424,371; Ind. Chim. Belge 39, 490-500 [1974]; Liebigs Ann. Chem. 716, 47-60 [1968]; European Patent 40,932; and Japanese Patent 46/3368, and the instructions for process (c) according to the invention).

Formula (IV) provides a general definition of the carboxylic acid esters required as starting substances for carrying out process (b) according to the invention. In this formula (IV), $R^9$ preferably represents a radical of the formula

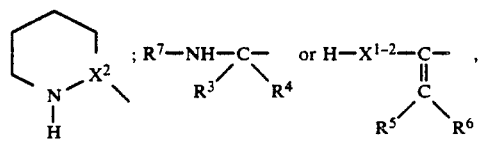

where
$X^{1-2}$ represents oxygen or a

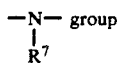

and $X^2$, $R^3$, $R^4$, $R^{5,}$ $R^6$ and $R^7$, preferably represent those radicals which have already been mentioned in connection with the description of the substances of the formula (I) according to the invention as being preferred for these substituents.

$R^{10}$ preferably represents straight-chain or branched alkyl having 1 to 4 carbon atoms, in particular represents methyl or ethyl.

The carboxylic acid esters of the formula (IV) are generally known compounds of organic chemistry or can be obtained in analogy to known processes (cf., for example, U.S. Pat. No. 4,730,006. Pestic. Sci. 16, 277-286 [1985]; Chem. Pharm. Bull. 32, 3934-3944 [1984]; Liebigs Ann. Chem. 1983, 1133-1151; Synthesis 1981, 915-917; Tetrahedron Lett. 22, 2485-2486 [1981]; Chem. Ber. 111,1058-1076 [1978]; Angew. Chem. 89, 344-345 [1977]; Chem. Ber. 110, 942-947 [1977]; Chem. Lett. 1976, 1095-1096; Angew. Chem. 88, 295-296 [1976]; DE 2,058,012; Bull. chem. Soc. Japan 44, 474-477 [1971]; J. chem. Soc. Perkin I, 1987, 877-884; DE 3,702,943; DE 2,331,549; J. Heterocycl. Chem. 6, 181-185, [1969]).

Formula (V) provides a general definition of the iso(thio)cyanates furthermore required as starting substances for carrying out process (b) according to the invention. In this formula (V), $R^1$, $R^2$ and $Z^1$ preferably represent those radicals which have already been mentioned in connection with the description of the substances of the formula (I) according to the invention as being preferred for these substituents.

The iso(thio)cyanates of the formula (V) are known or can be obtained in analogy to known processes (cf., for example, FR 2,003,438; ZA 67/3761 or CA70: 67 955d; European Patent 105,991; European Patent 67,689 or GB 1,336,871, and the Preparation Examples), for example when amines of the formula (III)

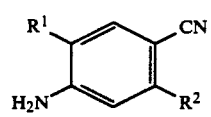 (III)

in which
$R^1$ and $R^2$ have the abovementioned meanings,
are reacted with phosgene, thiophosgene or diphosgene (Cl$_3$C-O-CO-Cl), if appropriate in the presence of a diluent, such as, for example, toluene, at temperatures between 20° C. and 120° C.

Formula (If) provides a general definition of the N-aryl-substituted nitrogen-containing heterocycles required as starting substances for carrying out process (c) according to the invention. In this formula (If), Het and $R^1$ preferably represent those radicals which have already been mentioned in connection with the description of the substances of the formula (I) according to the invention as being preferred for these substituents.

$R^{2-1}$ preferably represents fluorine, chlorine or bromine, in particular represents fluorine.

The N-aryl-substituted nitrogen-containing heterocycles of the formula (If) are compounds according to the invention and can be obtained with the aid of processes (a) or (b) according to the invention.

Formula (VI) provides a general definition of the alcohols or thiols furthermore required as starting substances for carrying out process (c) according to the invention. In this formula (VI), $Z^2$ and $R^8$ preferably represent those radicals which have already been mentioned in connection with the description of the substances of the formula (I) according to the invention as being preferred for these substituents.

The alcohols and thiols of the formula (VI) are generally known compounds of organic chemistry.

Formula (Ie) provides a general definition of the N-aryl-substituted nitrogen-containing heterocycles required as starting substances for carrying out process (d) according to the invention. In this formula (Ie), Het and $R^1$ preferably represent those radicals which have already been mentioned in connection with the description of the substances of the formula (I) according to the invention as being preferred for these substituents.

The N-aryl-substituted nitrogen-containing heterocycles of the formula (Ie) are compounds according to the invention and can be obtained with the aid of process (e) according to the invention.

Formula (VII) provides a general definition of the alkylating agents furthermore required as starting substances for carrying out process (d) according to the invention. In this formula (VII), $R^8$ preferably represents those radicals which have already been mentioned in connection with the description of the substances of the formula (I) according to the invention as being preferred for these substituents.

E represents a leaving radical which is customary for alkylating agents, preferably represents halogen, in particular represents chlorine, bromine or iodine, or represents in each case optionally substituted alkylsulphonyloxy, preferably having 1 to 4 carbon atoms, alkoxysulphonyloxy, preferably having 1 to 4 carbon atoms, or arylsulphonyloxy, preferably having 6 to 10 carbon atoms, such as, in particular, methanesulphonyloxy, trifluoromethanesulphonyloxy, methoxysulphonyloxy, ethoxysulphonyloxy or p-toluenesulphonyloxy.

The alkylating agents of the formula (VII) are generally known compounds of organic chemistry.

The N-aryl-substituted nitrogen-containing heterocycles of the formula (Ig), which are required as starting substances for carrying out process (e-α) according to the invention, are compounds according to the invention and can be obtained with the aid of processes (a), (b) or (c) according to the invention. In formula (Ig), $R^1$ and Het preferably represent those radicals which have already been mentioned in connection with the description of the substances of the formula (I) according to the invention as being preferred for these substituents, and $R^{8-1}$ represents allyl or benzyl.

The anhydrides of the formula (II) and the amines of the formula (IIIa), which are required as starting substances for carrying out process (e-β) according to the invention, have already been described above in connection with the description of the compounds of the formula (II) and (III). Some of the aminophenols of the formula (VIII), which are obtained when process (e-β) according to the invention is carried out, are known (cf., for example, Ind. J. Chem. 1613, 297–300 (1978); J. Org. Chem. 52, 144–149 (1987).

Suitable diluents for carrying out process (a) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or carboxylic acids, such as acetic acid or propionic acid.

If appropriate, process (a) according to the invention can be carried out in the presence of a suitable reaction auxiliary. Inorganic or organic acids, such as, for example, acetic acid or p-toluenesulphonic acid, anhydrides, such as, for example, acetic anhydride, or acid chlorides, such as acetyl chloride, are preferably used as reaction auxiliaries. It is also possible to use other customary water-eliminating agents, such as, for example, N,N′-dicyclohexylcarbodiimide, or customary acylation catalysts, such as, for example, 4-(N,N-dimethylamino)-pyridine, as reaction auxiliaries.

When carrying out process (a) according to the invention, the reaction temperatures can be varied within a relatively wide range. In general, the process is carried out at temperatures between 20° C. and 180° C., preferably at temperatures between 50° C. and 150° C.

For carrying out process (a) according to the invention, 1.0 to 1.5 moles, preferably 1.0 to 1.2 moles, of amine of the formula (III) and if appropriate 0.01 to 1.2 moles, preferably 0.1 to 1.0 mole, of reaction auxiliary are generally employed per mole of anhydride of the formula (II). The reaction is carried out and the reaction products are worked up and isolated by generally customary methods (cf. also the Preparation Examples).

Suitable diluents for carrying out process (b) according to the invention are inert organic solvents In particular, these include aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or alcohols, such as methanol, ethanol or propanol.

If appropriate, process (b) according to the invention is carried out in the presence of a reaction auxiliary which is suitable. Suitable reaction auxiliaries are all customary inorganic or organic bases. For example, these include alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicyclound-cene (DBU).

When carrying out process (b) according to the invention, the reaction temperatures can be varied within a relatively wide range. In general, the process is carried out at temperatures between 0° C. and 150° C., preferably at temperatures between 20° C. and 120° C.

For carrying out process (b) according to the invention, 0.5 to 5.0 moles, preferably 0.8 to 1.5 moles, of iso(thio)cyanate of the formula (V) and if appropriate 1.0 to 10.0 moles, preferably 1.0 to 5.0 moles, of reaction auxiliary are generally employed per mole of carboxylic acid ester of the formula (IV) or of a corresponding acid addition salt. Here, it is also possible to prepare the iso(thio)cyanates of the formula (V) in a preceding reaction from amines of the formula (III) and phosgene, thiophosgene or diphosgene ($Cl_3C$-O-CO-Cl) directly in the reaction vessel, and to react further the product with the carboxylic acid esters of the formula (IV), without isolation, as a "one-pot process".

The reaction is carried out and the reaction products are worked up and isolated by generally customary methods (cf. also the Preparation Examples).

Suitable diluents for carrying out process (c) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (c) according to the invention is preferably carried out in the presence of a reaction auxiliary which is suitable. Suitable reaction auxiliaries are all inorganic or organic bases which can customarily be employed. The hydrides, hydroxides, amides, alkoxides or carbonates of alkali metals, such as, for example, sodium hydride, sodium amide, sodium hydroxide, sodium methoxide, sodium ethoxide, potassium t-butoxide or potassium carbonate, or also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

When carrying out process (c) according to the invention, the reaction temperatures can be varied within a relatively wide range. In general, the process is carried out at temperatures between 0° C. and 150° C., preferably at temperatures between 20° C. and 120° C.

For carrying out process (c) according to the invention, 1.0 to 3.0 moles, preferably 1.0 to 1.5 moles, of alcohol or thiol of the formula (VI) and preferably 1.0 to 3.0 moles, preferably 1 0 to 2.0 moles, of reaction auxiliary are generally employed per mole of N-aryl-substituted nitrogen-containing heterocycle of the formula (If). The reaction is carried out and the reaction products are worked up and isolated by generally customary methods (cf. also the Preparation Examples).

Suitable diluents for carrying out process (d) according to the invention are inert organic solvents. Aliphatic, alicyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters, such as ethyl acetate, acids, such as acetic acid, nitriles, such as acetonitrile or propionitrile, amides, such as dimethylformamide, dimethylacetamide, N-methylpyrrolidone or hexamethylphosphoric triamide, are preferably used. If alkylating agents of the formula (VII) are used in the liquid form as reactants, it is also possible to employ the former at the same time as diluents, in appropriate excess.

Suitable reaction auxiliaries for carrying out process (d) according to the invention are all inorganic and organic bases which can customarily be used. The hydrides, hydroxides, amides, carbonates or hydrogen carbonates of alkali metals, such as, for example, sodium hydride, sodium amide, sodium hydroxide, sodium carbonate or sodium hydrogen carbonate, or also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

When carrying out process (d) according to the invention, the reaction temperatures can be varied within a relatively wide range. In general, the process is carried out between $-20°$ C. and $+150°$ C., preferably between 0° C. and $+100°$ C.

For carrying out process (d) according to the invention, 1.0 to 20.0 moles in each case, preferably 1.0 to 15.0 moles in each case, of alkylating agent of the formula (VII) and if appropriate 1.0 to 3.0 moles, preferably 1.0 to 2.0 moles, of reaction auxiliary are generally employed per mole of N-aryl-substituted nitrogen-containing heterocycle of the formula (Ie). The reaction is carried out and the reaction products of the formula (Id) are worked up and isolated by customary methods.

Suitable reducing agents for carrying out processes (e-α) and (e-β) according to the invention ($R^{8-1}$=benzyl) are all reducing agents which can customarily be used for reduction reactions of this type. Tris-triphenylphosphine-rhodiumchloride, tris-triphenylphosphine-palladium chloride or molecular hydrogen which is used in the presence of a customary hydrogenation catalyst, such as, for example, Raney nickel or palladium, are preferably used.

Suitable diluents for carrying out processes (e-α) and (e-β) according to the invention are all customary organic or inorganic solvents, depending on the reducing agent used. Ethers, such as diethyl ether, dioxane or tetrahydrofuran, alcohols, such as methanol, ethanol or propanol, carboxylic acids, such as acetic acid or propionic acid, or mixtures of the abovementioned solvents with carboxylic acids are preferably used.

Suitable reaction auxiliaries for carrying out process (e-α) and (e-β) according to the invention ($R^{8-1}$=benzyl) are all reaction auxiliaries which are customary for reactions of this type. Tertiary amines, such as, for example, pyridine, triethylamine, diazabicyclooctane (DABCO), diazabicyclononene (DBN) or diazabicycloundecene (DBU) are preferably used.

Acids which are employed for carrying out processes (e-α) and (e-β) according to the invention ($R^{8-1}$=allyl) are all customary acids which can be used for reactions of this type. Inorganic or organic acids, such as, for example, hydrochloric acid, sulphuric acid or nitric acid, or aliphatic or aromatic carboxylic acids, such as, for example, acetic acid, propionic acid or benzoic acid, or an acid ion exchanger are preferably used.

When carrying out process (e-α) and (e-β)/stage 2 according to the invention, the reaction temperatures can be varied within a relatively wide range depending on the reducing agent used. In general, the process is carried out at temperatures between 0 and 150° C., preferably between 20° and 120° C.

For carying out processes (e-α) and (e-β) according to the invention ($R^{8-1}$=benzyl), I mole to 5 moles, preferably 1 mole to 3 moles, of reducing agent and if appropriate 0.001 mole to 0.5 mole, preferably 0.05 mole to 0.3 mole, of catalyst and if appropriate catalytic amounts to 5 moles, preferably catalytic amounts to 3 moles, of reaction auxiliary are generally employed per mole of compound of the formula (I-g) or (IIIa), respectively.

For carrying out processes (e-α) and (e-β) according to the invention ($R^{8-1}$=allyl), 0.001 mole to 1 mole, preferably 0.05 to 0.5, of noble-metal catalyst and 0.1 mole to 5 moles, preferably 0.2 mole to 3 moles, of acid are generally employed per mole of the compound of the formula (Ig) of (IIIa), respectively.

Suitable diluents and reaction auxiliaries for stage 2 of process (e-β) according to the invention are the solvents and reaction auxiliaries already mentioned in the case of process (a).

When carrying out stage 2 of process (e-β) according to the invention, the reaction temperatures can be varied within a relatively wide range. In general, the process is carried out at temperatures between 20° C. and 180° C., preferably at temperatures between 50 C and 150° C.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the active compounds of the formula (I) according to the invention can be employed with particularly good success for combating monocotyledon and dicotyledon weeds in monocotyledon and dicotyledon crops, such as, for example, soy beans, cereals, corn, rice or cotton. The intermediates of the formula (VII) also possess a good herbicidal activity.

In suitable application rates, the active compounds according to the invention can also be employed as plant growth regulators, in particular as defoliants.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth and 9round synthetic minerals, such as highly disperse silica, alumina and silicates, as solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used as mixtures with known herbicides for controlling weeds, finished formulations or tank mixes being possible.

Suitable herbicides for the mixtures are known herbicides, such as, for example, l-amino-6-ethylthio-3-(2,2-dimethylpropyl)-1,3,5-triazine-2,4(1H,3H)-dione (AMETHY-DIONE) or N-(2-benzothiazolyl)-N,N'-dimethylurea (META-BENZTHIAZURON) for combating weeds in cereals; 4-amino-3-methyl-6-phenyl-1,2,4-triazin-5(4-H)-one (METAMITRON) for combating weeds in sugarbeets, and 4-amino-6-(1,1-dimethylethyl)-3-methylthio-1,2,4-triazin-5(4H)-one (METRIBUZIN) for combating weeds in soy beans. Mixtures with N-(methoxymethyl)-2,6-diethylchloroacetanilide (ALACHLOR); 2-ethyl-6-methyl-N-(1-methyl-2-methoxyethyl)-chloroacetanilide (METOLACHLOR); 5-(2-chloro-4-trifluoromethyl-phenoxy)-2-nitro-benzoic acid (ACIFLUORFEN); methyl5-(2,4-dichlorophenoxy)-2-nitrobenzoate(BIFENOX); 5-(2-chloro-4-trifluoromethyl-phenoxy)-N-methylsulphonyl-2-nitrobenzamide (FOMESAFEN); (2-ethoxy-1-methyl-2-oxo-ethyl)-5-[2-chloro-4-(trifluoromethyl)-phenoxy]-2-nitrobenzoate (LACTOFEN); (2-chloro-4-trifluoromethylphenyl]-(3-ethoxy-4-nitrophenyl) ether (OXYFLUORFEN); 2-[4,5-dihydro-4-methyl-4-isopropyl-5-oxo-(1H)-imidazol-2-yl]-5-ethyl-pyridine-3-carboxylic acid (IMAZETHAPYR); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); methyl 2-[[[[(4,6-dimethoxypyrimidin-2-yl)-amino]-carbonyl]-amino]-sulphonyl]-methyl]-benzoate (BENSULFURON); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)amino]-carbonyl}-benzenesulphonamide (CHLORSULFURON); 2-{[[((4-methoxy-6-methyl-1,3,5-triazin-2-yl)-amino)carbonyl]-amino]-sulphonyl}-benzoic acid or its methyl ester (METSULFURON); methyl 3-[[[[(4-methoxy-6-methyl-1,3,5-triazin-2-yl)-amino]-carbonyl]-amino]-sulphonyl]-thiophene-2-carboxylate (THIAMETHURON); 2-chloro-4-ethylamino-6-isopropylamino-1,3,5-triazine (ATRAZIN); 2-chloro-4-ethylamino-6-(3-cyanopropylamino]-1,3,5-triazine (CYANAZIN); 3-isopropyl-2,1,3-benzothiadiazin-4-one 2,2-dioxide (BENTAZONE); 4-amino-6-t-butyl-3-ethylthio-1,2,4-triazin-5(4H)-one (ETHIOZIN); 3-cyclohexyl-6-dimethylamino-1-methyl-1,3,5-triazine-2,4-dione (HEXAZINONE); and 2-[(2-chlorophenyl)-methyl]-4,4-dimethylisoxazolidin-3-one (DIMETHAZONE); are also possible Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

PREPARATION EXAMPLES

Example 1

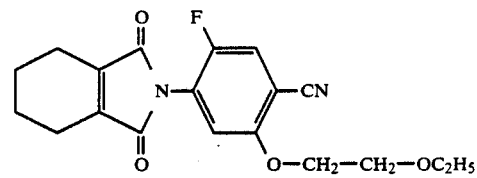

(Process a)

4.8 g (0.0214 mol) of 2-(2-ethoxyethoxy)-4-amino-5-fluorobenzonitrile and 3.8 g (0.025 mol) of 3,4,5,6-tetrahydrophthalic anhydride are heated at 100° C. for 2 hours in the presence of 0.57 g (0.003 mol) of p-toluenesulphonic acid, the cooled reaction mixture is taken up in 40 ml of tetrahydrofuran and stirred into aqueous sodium hydrogen carbonate solution, the mixture is extracted several times using dichloromethane, and the organic phase is dried over sodium sulphate, evaporated in vacuo and purified by chromatography on silica gel (eluent: cyclohexane/ethyl acetate 2:1). The resulting product may be recrystallized from ether/n-hexane.

3.04 g (40% of theory) of N-[4-cyano-5-(2-ethoxyethoxy)-2-fluorophenyl]-3,4,5,6-tetrahydrophthalimide of melting point 90° C. are obtained.

Example 2

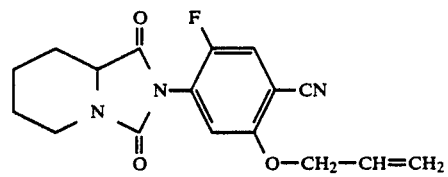

(Process b - one-pot process)

1.58 ml (0.013 mol) of diphosgene are added dropwise with stirring at 80° C. to 2.5 g (0.013 mol) of 2-allyloxy-4-amino-5-fluorobenzonitrile in 25 ml of absolute toluene, the mixture is subsequently refluxed for 4 hours, the toluene is then distilled off, the residue is again treated with 15 ml of absolute toluene and 2.2 ml (0.014 mol) of ethyl piperidine-2-carboxylate, 1 drop of diazabicycloundecene (DBU) is added, and the mixture is refluxed for 3 hours. When cold, the reaction mixture is filtered, the filtrate is evaporated in vacuo, and the residue is chromatographed over silica gel (eluent: cyclohexane/ethyl acetate 2:3) and subsequently recrystallized from ether/n-hexane.

b. 2.27 g (53% of theory) of 2-(5-allyloxy-4-cyano-2-fluorophenyl)-hexahydroimidazo[1,5-a]pyridine-1,3-dione of melting point 132° C. are obtained.

Example 3

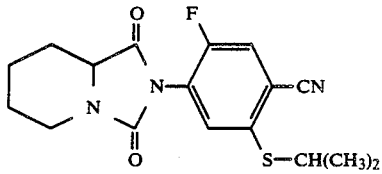

(Process c)

1.12 g (0.02 mol) of powdered potassium hydroxide and then 2-(4-cyano-2,5-difluorophenyl)-hexahydroimidazo[1,5-a]pyridine-1,3-dione) are added to 1.3 ml (0.014 mol) of isopropylmercaptan in 30 ml of absolute acetonitrile, the mixture is stirred at 40 C for 15 minutes and filtered, the filtrate is evaporated, and the residue is purified by chromatography on silica gel (eluent: dichloromethane/ethyl acetate 40:1) and recrystallization from ether/n-hexane.

1.72 g (38% of theory) of 2-(4-cyano-2-fluoro-5-isopropylthiophenyl)-hexahydroimidazo[1,5-a]pyridine-1,3-dione of melting point 61° C. are obtained.

Example 4

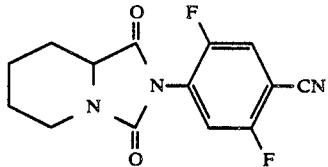

(Process b-one-pot variant)

6.05 ml (0.05 mol) of diphosgene are added dropwise at 80° C. in the course of 30 minutes to 7.7 g (0.05 mol) of 4-amino-2,5-difluorobenzonitrile in 100 ml of absolute toluene, and the mixture is subsequently refluxed for 5 hours. The solvent is subsequently distilled off, the residue is treated with 8.2 ml (0.052 mol) of ethyl piperidine-2-carboxylate in 50 ml of absolute toluene and 1 drop of diazabicycloundecene (DBU) and refluxed for 3 hours. When the solution is cold, the residue is filtered off with suction, and the filtrate is evaporated and chromatographed over silica gel (eluent cyclohexane/ethyl acetate 2:1).

9.55 g (65.6% of theory) of 2-(4-cyano-2,5-difluorophenyl)-hexahydroimidazo[1,5a]pyridine-1,3-dione of melting point 95° C. are obtained by recrystallization from toluene/n-hexane.

Example 5

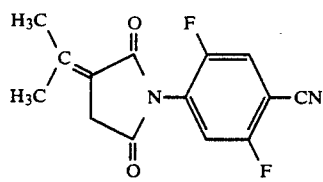

(Process a)

3.68 g (0.0263 mol) of 2-isopropylidenesuccinic anhydride and 3.85 g (0.025 mol) of 2,5-difluoro-4-aminobenzonitrile (cf. EP-A 224,001) in 70 ml of glacial acetic acid are heated at 135° C. for 5 hours, the mixture is subsequently evaporated, the residue is taken up in 30 ml of acetic anhydride and treated with 1.5 g (0.018 mol) of sodium acetate, and the mixture is heated at 90° C. for 2 more hours. For working up, the mixture is evaporated, the residue is distributed between dichloromethane and water, and the organic phase is washed with water, dried over sodium sulphate, evaporated in vacuo and purified by chromatography on silica gel.

2.54 g (36% of theory) of 1-(2,5-difluoro-4-cyanophenyl)-4-isopropylidene-pyrrolidine-2,5-dione of melting point 135° C. are obtained.

Example 6

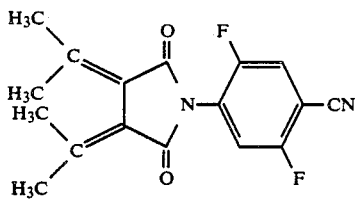

(Process a)

2.85 g (0.0158 mol) of 3,4-diisopropylidenesuccinic anhydride and 2.31 g (0.015 mol) of 2,5-difluoro-4-aminobenzonitrile (cf. EP-A 224,00) in 60 ml of glacial acetic acid are heated at 135° C. for 5 hours, the mixture is subsequently evaporated, the residue is taken up in 18 ml of acetic anhydride and treated with 0.9 g (0.011 mol) of sodium acetate, and the mixture is heated at 90° C. for 2 more hours. For working up, the mixture is evaporated, the residue is distributed between dichloromethane and water, and the organic phase is washed with water, dried over sodium sulphate, evaporated in vacuo and purified by chromatography on silica gel.

0.73 g (15.4% of theory) of 1-(2,5-difluoro-4-cyanophenyl)-3,4-diisopropylidene-pyrrolidine-2,5-dione of melting point 144° C. is obtained.

The following N-aryl-substituted nitrogen-containing heterocycles of the general formula (I) are obtained in a corresponding manner and in accordance with the general preparation instructions:

TABLE 1

(I)

Structure: R¹ and Het on one side, CN and R² on the other side of a benzene ring.

| Example No. | Het | R¹ | R² | physical properties |
|---|---|---|---|---|
| 7 | 3a,4,5,6,7,7a-hexahydro-1,3-dioxoisoindol-2-yl (cyclohexane-fused succinimide) | F | —OCF₃ | ¹H-NMR*): 1.85; 2.47; 7.39; 7.58; |
| 8 | 3,4-dimethyl-2,5-dioxo-2,5-dihydropyrrol-1-yl | F | —O—CH₂—CH=CH₂ | MS: m/e = 300[M⁺]; 260; 42 |
| 9 | hexahydroisoindole-1,3-dione | F | —O—CH₂—C(CH₃)=CH₂ | ¹H-NMR*): 1.85; 2.45; 6.88; 7.44 |
| 10 | hexahydroisoindole-1,3-dione | F | —O—CH₂—CH=CH—CH₃ | m.p. 18–121° C. |
| 11 | hexahydroisoindole-1,3-dione | F | —O—CH₂—CH=CH₂ | m.p. 126–127° C. |
| 12 | hexahydroisoindole-1,3-dione | F | —O—CH₂—CH(CH₃)—OC₂H₅ | m.p. 118–121° C. |
| 13 | hexahydroisoindole-1,3-dione | F | —O—CH₂—(tetrahydrofuran-2-yl) | m.p. 126–129° C. |
| 14 | hexahydroimidazo[1,2-a]pyridine-1,3-dione | F | —S—C(CH₃)₃ | m.p. 55° C. |

TABLE 1-continued $$\begin{array}{c} R^1 \quad CN \\ \diagup \diagdown \\ Het \quad R^2 \end{array} \quad (I)$$

| Example No. | Het | R¹ | R² | physical properties |
|---|---|---|---|---|
| 15 | hexahydropyrido[1,2-imidazoline-1,3-dione] | F | —O—CH$_2$—CH$_2$—OC$_2$H$_5$ | m.p. 112° C. |
| 16 | hexahydropyrido[1,2-imidazoline-1,3-dione] | F | —S—CH$_2$—(tetrahydrofuran-2-yl) | m.p. 105° C. |
| 17 | 3,4,5,6-tetrahydrophthalimide | F | —O—(CH$_2$)$_2$—O—(CH$_2$)$_2$—OC$_2$H$_5$ | m.p. 86° C. |
| 18 | hexahydropyrido[1,2-imidazoline-1,3-dione] | F | —O—(CH$_2$)$_2$—O—(CH$_2$)$_2$—O—C$_2$H$_5$ | m.p. 80° C. |
| 19 | 3,4,5,6-tetrahydrophthalimide | H | —O—CH$_2$—CH$_2$—OC$_2$H$_5$ | m.p. 108–115° C. |
| 20 | 3,4,5,6-tetrahydrophthalimide | F | F | m.p. 115° C. |
| 21 | 3,4,5,6-tetrahydrophthalimide | F | —O—CH$_2$—(tetrahydropyran-2-yl) | MS: m/e = 384(M$^+$); 356; 300; 85 |
| 22 | 3-isopropylidene-2,5-dioxopyrrolidinyl | F | —O—(CH$_2$)$_2$—O—(CH$_2$)$_2$—OC$_2$H$_5$ | m.p.: 80–85° C. |

TABLE 1-continued (I) [structure: benzene ring with R¹, CN, Het, R² substituents]

| Example No. | Het | R¹ | R² | physical properties |
|---|---|---|---|---|
| 23 | [3,4,5,6-tetrahydrophthalimide-N-yl] | F | —S—CH₂—COOC₂H₅ | |
| 24 | [3-(isopropylidene)-succinimide-N-yl] | F | —O—CH₂—CH=CH₂ | m.p.: 114° C. |
| 25 | [3-(isopropylidene)-succinimide-N-yl] | F | —OCH₂CH₂OC₂H₅ | |

*)The ¹H-NMR spectra were recorded in dueterochloroform (CDCl₃) with tetramethylsilane (TMS) as the internal standard. The chemical shift is indicated as δ value in ppm.

Example 26

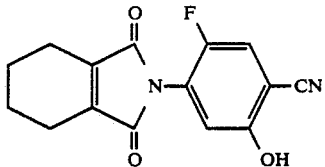

0.2 g (0.0002 mol) of tris-triphenylphosphine-rhodium chloride and 70 mg (0.0006 mol) of 1,4-diazabicyclo-[2,2,2]octane (DABCO) are added to 1 g (0.003 mol) of N-(2-fluoro-4-cyano-5-allyloxyphenyl)-3,4,5,6-tetrahydrophthalimide in 10 ml of 10 per cent aqueous ethanol, the reaction mixture is refluxed for 3 hours and subsequently (when cold) distributed between 30 ml of ether and 10 ml of 1 normal hydrochloric acid, the organic phase is separated off, dried over sodium sulphate and evaporated in vacuo, and 0.56 g (65% of theory) of N-(4-cyano-2-fluoro-5-hydroxyphenyl)-3,4,5,6-tetrahydrophthalimide are then obtained as a waxy solid.

MS: m/e (% relative intensity)=287 (16); 286 (61) [M+]; 108 (81); 80 (73); 79 100).

PREPARATION OF THE STARTING COMPOUNDS

Example VIII-1

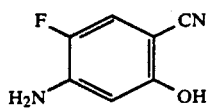

0.46 g (0.005 mol) of tris-triphenylphosphine-rhodium chloride and 0.36 g (0.0032 mol) of 1,4-diazabicyclo-[2,2,2]octane (DABCO) are added to 3 g (0.0156 mol) of 2-allyloxy-4-amino-5-fluorobenzonitrile in 50 ml of 10 per cent aqueous ethanol, the mixture is refluxed for 3 hours and then cooled, 100 ml of ether are added, the mixture is washed with 30 ml of water and dried over sodium sulphate, and the solvent is removed in vacuo.

0.4 g (17% of theory) of 4-amino-5-fluoro-2-hydroxybenzonitrile are obtained.

IR (pure): γ=3050–3530; 2260; 1635 cm⁻¹.

¹H-NMR (CD₃OD): δ=6.28 (d;1H; J=7Hz). 7.04 (d;1H; J=10.5 Hz).

Example III-1

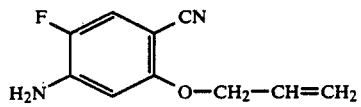

4.07 ml (0.06 mol) of allyl alcohol are added dropwise with stirring at room temperature to 1.8 g (0.06 mol) of sodium hydride in 30 ml of N-methylpyrrolidone, the mixture is subsequently stirred at room temperature for another 15 minutes, 4.62 g (0.03 mol) of 4-amino-2,5-difluorobenzonitrile are then added, the mixture is heated at 100° C. for one hour and then (when cold) stirred into ice-water and extracted several times with toluene, and the toluene phase is dried over sodium sulphate and evaporated in vacuo. The residue is purified by chromatography on silica gel (eluent: cyclohexane/ethyl acetate 3:1).

2 5 g (43% of theory) of 2-allyloxy-4-amino-5-fluorobenzonitrile are obtained as an oil.

$^1$H-NMR (CDCl$_3$/tetramethylsilane): δ=4.55 (m,2H); 5.3 (dd,1H), 5.44 (dd,1H); 6.0 (m,1H); 6.27 (d,1H); 7.1 (d,1H) ppm.

Example 111-2

F—[benzene ring with CN, H$_2$N, O—CH$_2$—CH$_2$—O—C$_2$H$_5$]

5.82 ml (0.06 mol) of 2-ethoxyethanol are added dropwise with stirring at room temperature to 1.8 g (0.06 mol) of sodium hydride in 30 ml of N-methylpyrrolidone, the mixture is subsequently stirred for another 15 minutes at room temperature, 4.62 g (0.03 mol) of 4-amino-2,5-difluorobenzonitrile are then added, the mixture is heated at 100° C. for one hour and then (when cold) stirred into ice-water and extracted several times with toluene, the toluene phase is dried over sodium sulphate and evaporated in vacuo. The residue is purified by chromatography on silica gel (eluent: cyclohexane/ethyl acetate 1:1).

3.5 g (52% of theory) of 2-(2-ethoxyethoxy)-4-amino-5-fluorobenzonitrile are obtained as an oil.

$^1$H-NMR (CDCl$_3$/tetramethylsilane): δ=1.22 (t,3H); 3.62 (q,2H); 3.8 (dd,2H); 4.1 (dd,4H]; 6.32 (d,1H); 7.1 (d,1H) ppm.

USE EXAMPLE

In the Use Example which follows the compound listed below was employed as comparison substance:

(A) [structure shown]

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive After three weeks, the degree of damage to the plants is rated in % damage in comparison to the development of the untreated control. The figures denote:

0%=no action (like untreated control)

100%=total destruction

In this test, for example, a clear superiority in the crop plant selectivity compared with the prior art is exhibited by the compounds of the following preparation examples: 1, 16 and 17.

It will be appreciated that the instant specification and claims are set forth by way of illustration and not limitation, and that various modifications and changes may be made without departing from the spirit and scope of the present invention.

What is claimed is:

1. An N-aryl-substituted nitrogen-containing heterocycle of the formula $$\text{(I)}$$

[structure: R$^1$ and Het on one side of benzene ring, CN and R$^2$ on the other]

in which

Het represents a heterocycle of the formula

[structure with X$^2$, N, Z$^1$, and ring]

R$^1$ represents hydrogen or halogen and

R$^2$ represents halogen, hydroxyl or represents a radical —Z$^2$—R$^8$, where

X$^2$ represents a CH group

Z$^1$ represents oxygen or sulphur,

Z$^2$ represents oxygen or sulphur,

R$^8$ represents in each case optionally substituted alkyl, alkenyl, alkinyl or cycloalkyl.

2. An N-aryl-substituted nitrogen-containing heterocycle according to claim 1, in which Het represents a heterocycle of the formula

[structure with X$^2$, N, Z$^1$, and ring]

R$^1$ represents hydrogen, fluorine, chlorine or bromine and

R$^2$ represents fluorine, chlorine, bromine, hydroxyl or represents a radical —Z$^2$—R$^8$, where X$^2$ represents a —CH— group, Z$^1$ represents oxygen or sulphur, Z$^2$ represents oxygen or sulphur, R$^8$ represents in each case straight-chain or branched alkyl having 1 to 8 carbon atoms, alkenyl having 2 to 8 carbon atoms, alkinyl having 3 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 3 to 8 carbon atoms and 1 to 13 identical or different halogen atoms, cyanoalkyl, alkoxyalkyl, alkylthioalkyl, halogenoalkoxyalkyl, alkoxyalkoxyalkyl, bis-(alkoxy)alkyl, bis-(alkylthio)alkyl, alkylcarbonylalkyl, alkoxycarbonylalkyl or alkoxyalkoxycarbonylalkyl, each having 1 to 8 carbon atoms in the individual alkyl moieties and if appropriate 1 to 9 identical or different halogen atoms, or represents cycloalkyl, cycloalkyloxycarbonylalkyl or cycloalkylalkyl, each of which has 3 to 7 carbon atoms in the cycloalkyl moiety and if appropriate 1 to 4 carbon atoms in the straight-chain or branched alkyl moiety and each of which is optionally substituted on the cycloalkyl moiety by identical or different substituents selected from the group consisting of halogen as well as in each case straight-chain or branched alkyl or alkoxy, each having 1 to 4 carbon atoms, $R^8$ furthermore also represents oxetanylalkyl, tetrahydrofuranylalkyl or tetrahydropyranylalkyl, each of which has 1 to 3 carbon atoms in the respective alkyl moieties and each of which is optionally substituted by alkyl having 1 to 4 carbon atoms, and represents aralkyl which has 6 to 10 carbon atoms in the aryl moiety and 1 to 4 carbon atoms in the straight-chain or branched alkyl moiety and is optionally substituted on the aryl moiety by identical or different substituents selected from the group consisting of halogen, cyano, nitro, in each case straight-chain or branched alkyl, alkoxy, alkylthio or alkoxycarbonyl, each having 1 to 4 carbon atoms, or in each case straight-chain or branched halogenoalkyl, halogenoalkoxy or halogenoalkylthio, each having 1 to 4 carbon atoms and 1 to 9 identical or different halogen atoms.

3. An N-aryl-substituted nitrogen-containing heterocycle according to claim 1, in which Het represents a heterocycle of the formula

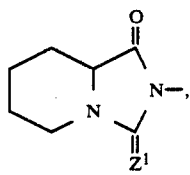

$R^1$ represents hydrogen, fluorine or chlorine and
$R^2$ represents fluorine, chlorine or represents a radical $-Z^2-R^8$,
$Z^1$ represents oxygen or sulphur,
$Z^2$ represents oxygen or sulphur,
$R^8$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, furthermore represents in each case straight-chain or branched halogenoalkyl having 1 to 4 carbon atoms or halogenoalkenyl having 3 to 5 carbon atoms and in each case 1 to 8 identical or different halogen atoms, or represents in each case straight-chain or branched cyanoalkyl, alkoxyalkyl, alkylthioalkyl, halogenoalkoxyalkyl, alkyl, alkoxyalkoxyalkyl, alkylcarbonylalkyl, alkoxycarbonylalkyl or alkoxyalkoxycarbonylalkyl, each having 1 to 5 carbon atoms in the individual alkyl moieties, furthermore represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, in each case optionally monosubstituted to trisubstituted by identical or different substituents from the group consisting of methyl, methoxy, fluorine and chlorine, or represents oxetanylmethyl, oxetanylethyl, tetrahydrofuranylmethyl, tetrahydrofuranylethyl, tetrahydropyranylmethyl and tetrahydropyranylethyl, in each case optionally substituted by methyl or ethyl, or represents benzyl or phenylethyl, in each case optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy and trifluoromethylthio.

4. An N-aryl-substituted nitrogen-containing heterocycle according to claim 3, in which
$R^2$ represents hydroxyl.

5. A compound according to claim 1, wherein such compound is N-[4-cyano-5-(fur-2-yl-methylthio)-2-fluorophenyl]-hexahydroimidazo[1,5-a]pyridine-1,3-dione of the formula

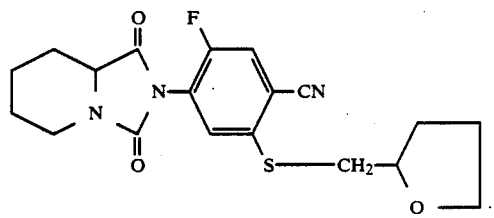

6. A herbicidal composition comprising a herbicidally effective amount of a compound according to claim 1 and a diluent.

7. A method of combating unwanted vegetation which comprises applying to such vegetation or to a locus from which is is desired to exclude such vegetation a herbicidally effective amount of a compound according to claim 1.

8. A compound according to claim 1, wherein such compound is 2-(5-allyloxy-4-cyano-2-fluorophenyl)-hexahydroimidazo [1,5-a]pyridine-1,3-dione of the formula

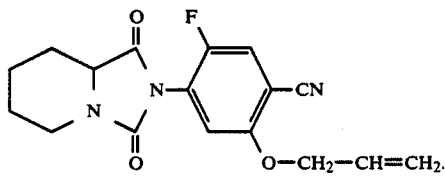

9. A compound according to claim 1, wherein such compound is 2-(4-cyano-2-fluoro-5-isopropylthiophenylhexahydroimidazo [1,5-a]pyridine-1,3-dione of the formula

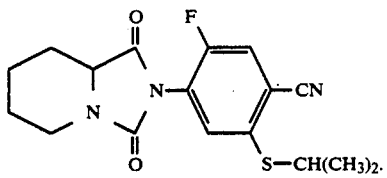

10. A compound according to claim 1, wherein such compound is 2-(4-cyano-2,5-difluorophenyl)-hexahydroimidazo[1,5-a]pyridine-1,3-dione of the formula

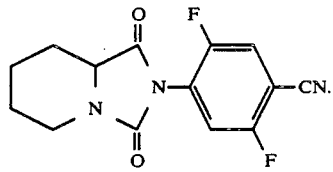

11. A compound according to claim 1, wherein such compound is N-[4-cyano-5-(t-butyl-thio)-2-fluorophenyl]-hexahydroimidazo[1,5-a]pyridine-1,3-dione of the formula

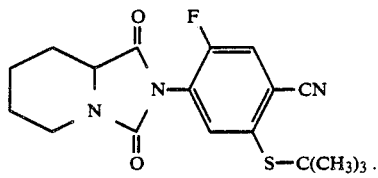

12. A compound according to claim 1, wherein such compound is N-[4-cyano-5-(ethoxy-2-ethoxy)-2-fluorophenyl]-hexahydroimidazo[1,5-a]pyridine-1,3-dione of the formula

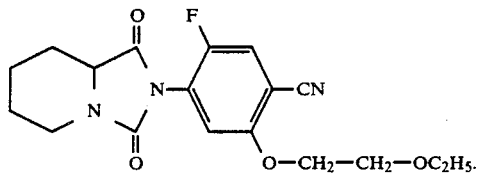

13. A compound according to claim 1, wherein such compound is N-[4-cyano-5-(ethoxy-2-ethoxy-2-ethoxy)-2-fluorophenyl]-hexahydroimidazo[1,5-a]pyridine-1,3-dione of the formula

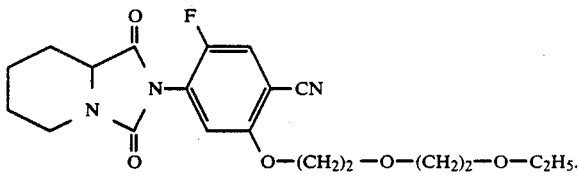

14. The method according to claim 7, wherein such compound is
N-[4-cyano-5-(fur-2-yl-methylthio)-2-fluorophenyl]-hexahydroimidazo[1,5-a]pyridine-1,3-dione,
2-(5-allyloxy-4-cyano-2-fluorophenyl)-hexahydroimidazo[1,5-a]pyridine-1,3-dione,
2-(4-cyano-2-fluoro-5-isopropylthiophenylhexahydroimidazo[1,5-a]pyridine-1,3-dione,
2-(4-cyano-2,5-difluorophenyl)-hexahydroimidazo[1,5-a]pyridine-1,3-dione,
N-[4-cyano-5-(t-butyl-thio)-2-fluorophenyl]-hexahydroimidazo[1,5-a]pyridine-1,3-dione,
N-[4-cyano-5-(ethoxy-2-ethoxy)-2-fluorophenyl]-hexahydroimidazo[1,5-a]pyridine-1,3-dione, or
N-[4-cyano-5-(ethoxy-2-ethoxy-2-ethoxy)-2-fluorophenyl]-hexahydroimidazo[1,5-a]pyridine-1,3-dione.

* * * * *